United States Patent
Darwish et al.

(10) Patent No.: US 8,517,730 B2
(45) Date of Patent: Aug. 27, 2013

(54) TOOTH EXTRACTION TOOL

(75) Inventors: Saied Mohamed Hassan Darwish, Riyadh (SA); Abdel Nasser Dawood, Riyadh (SA); Gamal Mohamed Hassan Darwish, Alexandria (EG); Abdulrahman M. Al-Ahmari, Riyadh (SA)

(73) Assignee: King Saud University, Riyadh (SA)

( * ) Notice: Subject to any disclaimer, the term of this patent is extended or adjusted under 35 U.S.C. 154(b) by 9 days.

(21) Appl. No.: 12/650,624

(22) Filed: Dec. 31, 2009

(65) Prior Publication Data

US 2011/0159459 A1    Jun. 30, 2011

(51) Int. Cl.
*A61C 1/07* (2006.01)

(52) U.S. Cl.
USPC ............................................... 433/118

(58) Field of Classification Search
USPC ......... 433/103–135, 141, 148–151, 153–162; 81/384–414, 463–464, 57.4, 9.22; 7/125–137
See application file for complete search history.

(56) References Cited

U.S. PATENT DOCUMENTS

| | | | | |
|---|---|---|---|---|
| 1,464,824 A * | 8/1923 | Kollock et al. | ............ | 74/55 |
| 1,702,487 A * | 2/1929 | Vasko | ............ | 433/25 |
| 2,027,470 A * | 1/1936 | Caruso | ............ | 433/158 |
| 2,030,798 A * | 2/1936 | Krajeski | ............ | 433/159 |
| 2,245,856 A * | 6/1941 | Glas | ............ | 72/450 |
| 2,396,562 A * | 3/1946 | Forss | ............ | 72/407 |
| 2,428,689 A * | 10/1947 | Sykes | ............ | 433/47 |
| 2,777,198 A * | 1/1957 | Wallace | ............ | 433/118 |
| 2,848,812 A * | 8/1958 | Fuest | ............ | 433/121 |
| 2,977,683 A * | 4/1961 | Wiltse | ............ | 433/98 |
| 3,332,149 A * | 7/1967 | Mumaw | ............ | 433/2 |
| 3,332,150 A * | 7/1967 | Mumaw | ............ | 433/24 |
| 3,456,349 A * | 7/1969 | Heimann | ............ | 433/153 |
| 3,468,031 A * | 9/1969 | Mumaw | ............ | 433/146 |
| 3,786,550 A * | 1/1974 | Jones | ............ | 29/238 |
| 3,827,148 A * | 8/1974 | Diliberto | ............ | 433/122 |
| 4,669,979 A * | 6/1987 | Snead | ............ | 433/4 |
| 4,880,382 A * | 11/1989 | Moret et al. | ............ | 433/118 |
| 5,209,747 A * | 5/1993 | Knoepfler | ............ | 606/16 |
| 5,253,382 A * | 10/1993 | Beny | ............ | 15/22.1 |
| 5,269,291 A * | 12/1993 | Carter | ............ | 606/128 |
| 5,518,008 A * | 5/1996 | Cucchiaro et al. | ............ | 600/590 |
| 5,547,380 A * | 8/1996 | Goodman | ............ | 433/215 |
| 5,579,786 A * | 12/1996 | Wolk et al. | ............ | 132/322 |
| 5,625,916 A * | 5/1997 | McDougall | ............ | 15/28 |
| 5,636,988 A * | 6/1997 | Murayama | ............ | 433/118 |
| 5,755,573 A * | 5/1998 | LeBlanc | ............ | 433/159 |
| 5,758,729 A * | 6/1998 | Undin | ............ | 173/11 |
| 6,347,425 B1 * | 2/2002 | Fattori et al. | ............ | 15/22.1 |
| 7,021,932 B2 * | 4/2006 | Standish | ............ | 433/157 |
| 7,128,571 B2 * | 10/2006 | Young | ............ | 433/3 |
| 2004/0043359 A1 * | 3/2004 | Gould et al. | ............ | 433/153 |
| 2004/0229190 A1 * | 11/2004 | Gould et al. | ............ | 433/153 |
| 2005/0008987 A1 * | 1/2005 | Standish | ............ | 433/153 |

(Continued)

*Primary Examiner* — Cris L Rodriguez
*Assistant Examiner* — Matthew Saunders
(74) *Attorney, Agent, or Firm* — Lowe Hauptman Ham & Berner, LLP

(57) ABSTRACT

A tooth extracting tool including an elongated handle and a pair of tooth engaging members extending out of one end of the handle and a pneumatic or hydraulic piston for tightly gripping the tooth to be extracted between the pair of tooth engaging members. The tool also includes a mechanism for subjecting the grasped tooth to linear oscillation at an opposite end of the handle and for limiting the back and forth linear movement of the tooth to between about plus or minus 5 mm.

1 Claim, 2 Drawing Sheets

(56) References Cited

U.S. PATENT DOCUMENTS

2005/0266376 A1* 12/2005 Sokol et al. ............... 433/118
2005/0282110 A1* 12/2005 Goodman et al. .......... 433/118
2006/0014119 A1* 1/2006 Bouneff ..................... 433/118
2008/0008979 A1* 1/2008 Thomas et al. .............. 433/80
2008/0010770 A1* 1/2008 Hegemann et al. ......... 15/167.1
2008/0277128 A1* 11/2008 Satou ........................ 173/48

* cited by examiner

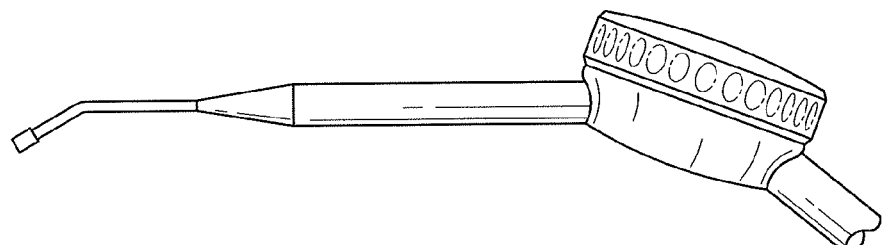
FIG. 4
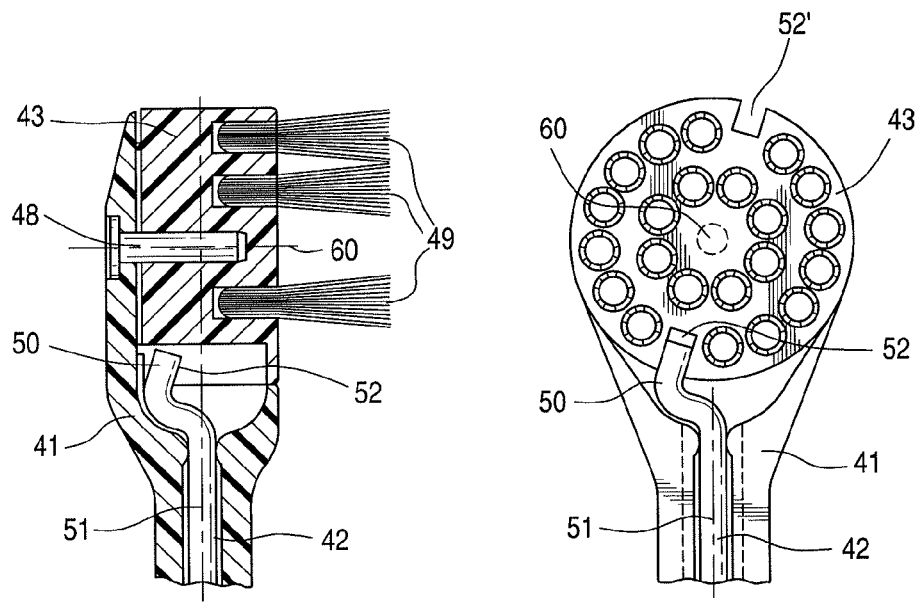
FIG. 5
PRIOR ART
FIG. 6
PRIOR ART

TOOTH EXTRACTION TOOL

FIELD OF THE INVENTION

This invention relates to a tooth extraction tool and more particularly to a tooth extraction tool that subjects a tooth to be extracted to linear oscillation.

BACKGROUND FOR THE INVENTION

Tooth extraction tools are will known and have been in use for many years. For example, a U.S. Pat. No. 2,777,198 of Wallace discloses a tooth extraction device which provides a minimum danger of injury to the tooth or to the jaw of a patient. The device uses a pair of forceps which are connected to an arm. Then after the forceps are engaged with a tooth, a motor is activated to transmit a high frequency vibration through the forceps to the tooth. The vibration causes the breaking down of the tissue surrounding the tooth so that slight upward or downward movement of the arm removes the tooth from an upper or lower dental arch.

A more recent U.S. Pat. No. 4,230,454 of Lococo discloses a tooth extractor that utilizes a vice type grip member having a joint member engaged by a forked end of a lever. The lever has a convexly curved fulcrum surface that rests against a planar base plate located on a patient's teeth that are adjacent to the tooth that is to be extracted. The grip member has two hemispherical tips for engaging correspondingly shaped indentations drilled in the buccal and lingual side of the tooth.

A more recent approach to the removal of teeth is disclosed in a U.S. Pat. No. 7,303,395 of Hornig et al. As disclosed an extractor has a first and a second lever and a first and second branch pivotably connected to each other by a hinge. A rod for mechanically and manually adjusting the first and second levers is provided. An extracting part includes at least one resistance element for anchoring the tooth and includes a first support for coupling with a receiving part of the first branch. A second support is placed against the extractor and has an opening for the extracting part.

Notwithstanding the above, it is presently believed that there is a need for an improved device for facilitating the extraction of a tooth and a potential commercial market for a tooth extraction tool in accordance with the present invention. There should be a demand and a commercial market for such devices because such devices significantly reduce the muscular strength required to extract a tooth and therefore reduce the stress and fatigue of a dentist as well as the stress on a patient. In addition, the cost for a dental extraction tool in accordance with the present invention is a relatively small cost in view of its advantages and the tool itself is relatively durable. Further, the device in accordance with the present invention should reduce the likelihood of crushing a tooth as well as problems associated with removing the roots and pieces of a crushed tooth.

Further, the tools in accordance with the present invention expand on the motion applied by the forceps to luxate or loosen teeth and expand the socket of the tooth. Further, the apical pressure results in minimal movement of the tooth in an apical direction and exposure of the tooth socket by the break down in the periodontal ligament space. In addition, the fulcrum, the center of the tooth's movement is placed more apically and decreases the likelihood of fracturing the root. This results in expansion of the buccal plate and lingual apical pressure aimed at expanding the lingual crestal structure. Advantageously the linear pressure moves the tooth which causes some internal expansion of the tooth socket (single conical roots).

BRIEF SUMMARY OF THE INVENTION

In essence the present invention contemplates a tooth extraction tool that includes a longitudinally extending handle and a pair of tooth engaging members for engaging the tooth to be extracted, extending outwardly at one end of the handle on one side thereof. The tooth extracting members engage the tooth on opposite sides thereof and a fluid activated piston is operatively connected to one of the tooth engaging members to tightly grip a tooth to be extracted between the two engaging members. The tool also includes means for subjecting the tightly gripped tooth to linear oscillation or forward and backward vibration about a generally longitudinal axis of the clamped tooth. This later means is constructed and arranged at the opposite end of the handle.

The invention will now be described in connection with the accompanying drawings wherein like reference numerals have been used to define like parts.

DESCRIPTION OF THE DRAWINGS

FIG. 4 is a side elevational view of a polishing tool of the type commonly used in a dental office and which provides linear oscillation to a tooth.

FIG. 5 is a cross sectional side view illustrating a part of a toothbrush; and

FIG. 6 is a sectional view of the tooth brush shown in FIG. 2.

DESCRIPTION OF THE PREFERRED EMBODIMENTS OF THE INVENTION

Figure 1:
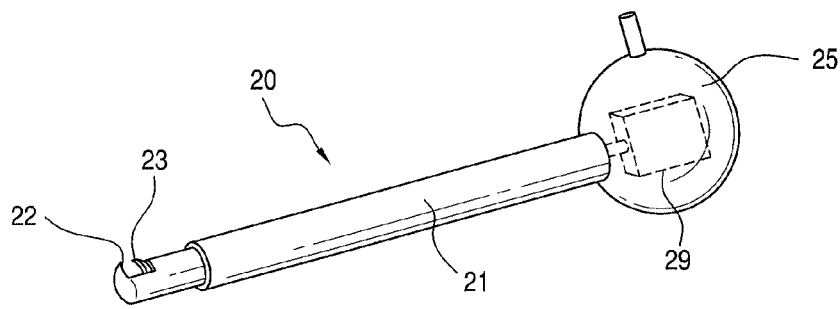
FIG. 1 is an isometric view of a tooth extracting tool in accordance with a preferred embodiment of the invention.
Figure 2:
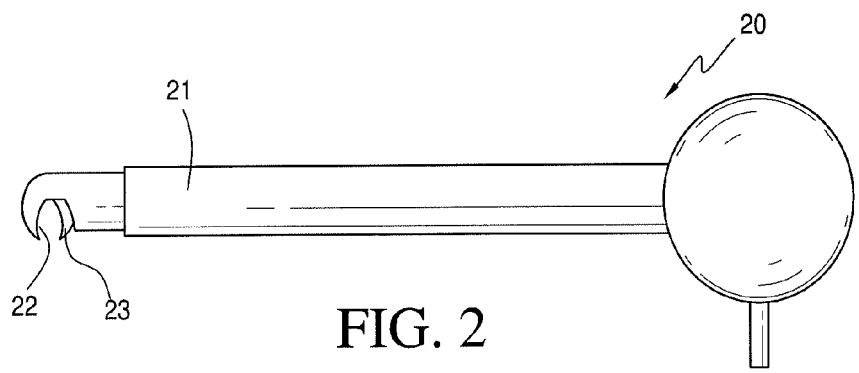
FIG. 2 is a top or plan view of the tooth extraction tool shown in FIG. 1.

As shown in FIGS. 1 and 2, a tooth extraction tool 20 comprises or consists of an elongated handle 21 and a pair of forceps or tooth engaging members at one end of the handle. The forceps include two tooth engaging members 22 and 23 one of which is fixed and the other of which is movable to tightly grip a tooth to be removed between the two members. The first of the tooth engaging members 22 is fixed while the second member 23 moves toward and away from the first member 22 to tightly grip a tooth (not shown) that is to be removed. The second removable tooth engaging member is moved by a fluid actuated piston 24 to tightly grip the tooth and subsequently after removal to release the tooth.

Figure 3:
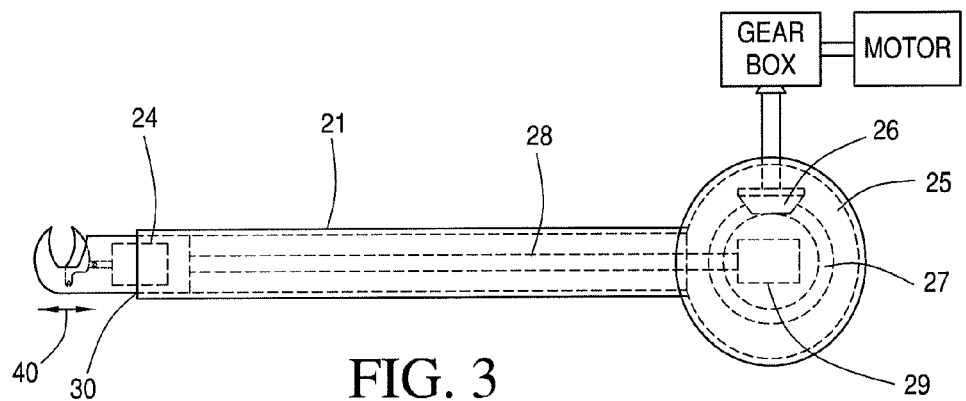
FIG. 3 is a bottom view of the tooth extraction tool shown in FIGS. 1 and 2, but illustrating a fluid activated piston, handle and rod extending through the handle for providing linear oscillation to a tooth to be removed.

The tooth engaging members 22 and 23 grip a tooth to be removed in response to the fluid activated piston 24. The fluid may be applied hydraulically or pneumatically. As shown, the tooth extraction tool 20 also includes a housing 25 at an opposite end of the handle 21. The housing 25 encases a pair of conical gears 26 and 27, one of which is a driving gear 26 and the other a driven gear 27 (see FIG. 3). The driven gear 27 rotates a rod 28 through a gear box 29 to provide linear oscillation to the tooth engaging members 22 and 23 about a pivot 30. In the preferred embodiment of the invention the linear oscillation is provided by a dentist's polishing tool as shown in FIG. 4. The polishing tool may for example be a model.: PROPJET-2 manufactured by Suzhou Dentasia Medical Equipment Co., Ltd. of China. The rotational movement of the rod 28 rotates an eccentric (not shown) to produce linear back and forth movement to the members 22 and 23 as shown by the arrow 40.

It should be recognized that the linear oscillation may be provided by a number of conventional mechanisms as for example disclosed in a U.S. Pat. No. 5,625,916 all of the details of which are incorporated herein in their entirety by reference. As disclosed in the patent, a drive shaft is rotated by a motor drive. The drive shaft terminates in an off set crank end which is located in a slot or opening in a block so that the 360° rotation of a shaft is transmitted into a linear back and forth movement.

A further example of linear oscillation may be provided by an electric motor with a coil arrangement for providing oscillatory rotational movement is disclosed in a U.S. Pat. No. 7,554,225 of Kraus et al. which is incorporated herein in its entirety by reference. As disclosed therein, an electric motor includes at least one oscillatory motor component, a magnetic arrangement having at least one permanent magnet and a coil for generating a magnetic field. During the interaction between the magnet arrangement and the magnetic field provided by the coil, a torque for generating an oscillatory movement is generated.

As illustrated in FIGS. 5 and 6 a toothbrush includes a head section 41, a rotatable shaft 42 that extends from a handle to head section 41 and rotates about a longitudinal axis 51. This rotation of the shaft 42 oscillates the circular bristle holder 43 back and forth about a pivot pin or rod 48. The head section 41 supports the rod 48 that lies on a transverse axis 60. One end 50 of the shaft 42 has an integrally formed remote most end 52 that is offset from the longitudinal axis 51.

The remote most end 52 fits into a slot 52' formed in a side of the bristle holder 48. The bristle holder 43 also includes a plurality of bristle clusters 49. The end 50 points toward an intersection of the longitudinal axis 51 and the lateral axis 60 of the rod 48. When the shaft 42 is rotated, the remote end 52 drivingly engages the slot 52' to cause the bristle holder 43 to vibrate or move back and forth about the pivot pin or rod 48 thus the holder 43 rotates forward and backward about the rod 48 and provides the relative motion between the head section 41 and the bristles 49.

The linear motion translated from a rotational motion in the present invention is adapted to move the tooth engaging member and the tooth clamped therein through a linear displacement of between plus and minus 5 mm until most of the ligaments binding the tooth in its socket are broken. Then the tooth can be lifted out of the socket using the leverage provided by the handle.

While the invention has been disclosed in connection with its preferred embodiments it should be recognized that changes and modifications may be made therein without departing from the scope of the appended claims.

What is claimed is:

1. A tooth extraction tool consisting of:
an elongated handle;
a housing linearly movably disposed within said elongated handle at one end thereof;
a pair of tooth engaging members for engaging a tooth to be extracted by gripping a tooth to be extracted on opposite sides thereof;
wherein one of said tooth engaging members is integral with and fixed to said housing, and the other of said tooth engaging members is movable with respect to said fixed tooth engaging member;
a pneumatically activated piston disposed within said housing and operatively connected to said movable tooth engaging member to tightly grip a tooth to be extracted between said tooth engaging members;
an oscillator for linearly oscillating said housing and providing linear oscillation to a gripped tooth, said oscillator consisting of a motor, a gear box and a pair of conical gears, a connecting rod extending through said handle and connected to said housing at one end thereof, an eccentric connected to said connecting rod for providing back and forth linear oscillation to said tooth engaging members and a tooth gripped by said tooth engaging members and wherein said linear oscillation is limited to a movement of between about plus or minus 5 mm and wherein said linear oscillation is provided by a dental polishing tool.

* * * * *